(12) United States Patent
Vea et al.

(10) Patent No.: US 6,538,014 B1
(45) Date of Patent: Mar. 25, 2003

(54) PROCESS FOR THE AGGROCHEMICAL TREATMENT OF RANGELANDS

(75) Inventors: Ely Vea, Raleigh, NC (US); Francois Colliot, Fontaines Saint Martin (FR)

(73) Assignee: Bayer CropScience, Inc., Lyon Cedex (FR)

( * ) Notice: Subject to any disclaimer, the term of this patent is extended or adjusted under 35 U.S.C. 154(b) by 0 days.

(21) Appl. No.: 08/369,865

(22) Filed: Jan. 6, 1995

Related U.S. Application Data

(63) Continuation of application No. 08/202,673, filed on Feb. 25, 1994, now abandoned, which is a continuation of application No. 07/963,115, filed on Oct. 19, 1992, now abandoned.

(51) Int. Cl.$^7$ .............................................. A01N 43/56
(52) U.S. Cl. ........................................ 514/407; 514/404
(58) Field of Search ................................ 514/404, 407

(56) References Cited

U.S. PATENT DOCUMENTS 5,232,940 A * 8/1993 Hatton et al. ............... 514/407

FOREIGN PATENT DOCUMENTS

EP   0295117   * 12/1988

OTHER PUBLICATIONS

Buntain et al, C.A.; vol. 112 (1990) 112: 35, 845m.*

* cited by examiner

*Primary Examiner*—Jose' G. Dees
(74) *Attorney, Agent, or Firm*—Morgan & Finnegan, L.L.P.

(57) ABSTRACT

A process for the treatment of grasslands against insects, comprising applying an effective quantity of 1-[2,6-dichloro-4-(trifluoromethyl)phenyl]-3-cyano-4-[(trifluoromethyl)-sulphinyl]-5-aminopyrazole to the grasslands.

7 Claims, No Drawings

PROCESS FOR THE AGGROCHEMICAL TREATMENT OF RANGELANDS

This is continuation of application Ser. No. 08/202,673, filed on Feb. 25, 1994 both now abandoned which is a continuation of application Ser. No. 07/963,115, filed on Oct. 19, 1992 abandoned.

The present invention relates to a new process for the treatment of grasslands using an insecticide product, and more particularly relates to a new process for the treatment of grasslands against locusts and grasshoppers.

Grasslands, which are known in English as rangelands, or which are also called pampas, are the object of periodic invasion by locusts and grasshoppers. These are grassy zones and are attractive to locusts.

Although the insecticides available on the market and in the literature are very numerous, there is no satisfactory solution to the above-mentioned problem. Even worse, an insecticide having a certain effectiveness recognized at present is dieldrin, which is used in a rather large amount and which is now prohibited. Given that this insecticide was more or less the only one that was effective, it was able to obtain waivers authorizing its use in spite of the initial temporary prohibition. These waivers authorizing temporary use have been renewed several times, which indeed shows the intensity of the problem that needs to be solved and the absence of a solution by the means known in themselves.

A new process for the treatment of grasslands has now been found, which conveniently and economically solves the problems of attacks of the grasslands by locusts and grasshoppers.

The process according to the present invention is characterized by the fact that one applies to the grasslands attacked, or susceptible to attack, by grasshoppers or locusts (Schistocerca spp.), an effective quantity of-product A, which consists of 1-[2,6-dichloro-4-$CF_3$-phenyl)-3-cyano-4-$CF_3SO$-5-$NH_2$-pyrazole.

More precisely, the process according to the invention is particularly suited for grasslands attacked or susceptible to attack by grasshoppers of the type Melanoplus spp. and/or of locusts of the type Schistocerca sppo, particularly *Schistocerca gregaria* or those of the type *Chortoicetes terminifera*.

Product A has been known, particularly through the application for European Patent No. 295117, but it has been known for having a vast range of very diverse activities. Given that the particular problem of the grasslands has in practice not been solved by any insecticide, the specialist has had no reason to think about orienting himself particularly towards this product A any more than towards other products.

According to a preferred aspect of the invention, one applies an effective quantity of active material A to the ground, generally in the form of a fluid or solid composition, preferably in liquid form. The application is done by spraying of the liquid or by dispersion of the solid form. The use of a liquid formulation is preferred for the treatment of large surfaces.

The compositions used in the invention are generally dilute compositions that contain 0.001 to 95% of active material A, preferably 0.2 to 15% of active material. The rest of the composition generally consists of a liquid or solid support, as well as possibly of additives such as surfactants or others. These compositions are prepared by any means known in itself, particularly according to the techniques described in European Patent No. 295117.

According to another preferred aspect of the invention, one applies a quantity between 2 and 50 g/ha of active material, preferably between 3 g/ha and 20 g/ha.

The following examples, given on a nonlimiting basis, illustrate the invention and show how it can be used.

The abbreviation JAT means "days after the treatment."

EXAMPLE 1

A zone of grassland is treated under controlled conditions, using cages to limit the space of movement of the insects. This zone is infested at a rate of 40 grasshoppers (*Melanoplus sanguinipes*) per $m^2$. For experimental purposes, the infestation is renewed 2 days before each observation of the effectiveness of the products, without performing a new insecticide treatment. The results are observed by performing mortality measurements (=percentage of grasshoppers killed). A remarkable persistence of action is observed.

| Grams of Product A per hectare | Effectiveness (%) against the grasshopper *Melanoplus Sanquinipes* | | | |
|---|---|---|---|---|
| | Immediate Action | Persistence of Action | | |
| | 1 DAT | 7 DAT | 15 DAT | 28 DAT |
| 6.2 | 87 | 98 | 93 | 38 |
| 12.5 | 93 | 100 | 100 | 69 |
| 25 | 98 | 100 | 100 | 93 |

EXAMPLE 2

A zone of grassland infested at a rate of 40 locusts (*Chortoicetes terminifera*) per m2 is treated, and the infestation is renewed 2 days before each effectiveness measurement. The results are observed by performing mortality measurements (=percentage of locusts killed). A remarkable persistence of action is observed.

| Gram of product A per hectare | Effectiveness (%) against the locust *Chortoicetes terminifera* | | | | | |
|---|---|---|---|---|---|---|
| | Immediate Action 1 DAT | | Persistence of action | | | |
| | Nymphs | Adults | 5 DAT | 10 DAT | 20 DAT | 30 DAT |
| 3.1 | 70 | 58 | 96 | 90 | 74 | 55 |
| 6.25 | 100 | 93 | 100 | 98 | 93 | 80 |
| 12.5 | 100 | 100 | 100 | 100 | 96 | 82 |
| 25 | 100 | 100 | 100 | 100 | 100 | 96 |

EXAMPLE 3

One treats a zone of grassland infested at a rate of 40 locusts (*Schistocerca gregaria*) per $m^2$. For experimental purposes, the infestation is renewed 2 days before each effectiveness measurement. The results are observed by performing mortality measurements (=percentage of locusts killed). A remarkable persistence of action is observed.

| Gram of product | Effectiveness (%) against the locust (*Schistocerca gregaria*) | | | | |
|---|---|---|---|---|---|
| A per hectare | Immediate Action | | Persistence of action | | |
| | 1 DAT | 2 DAT | 7 DAT | 14 DAT | 18 DAT |
| 2.5 | 58 | 72 | 88 | 72 | 56 |
| 5 | 82 | 93 | 100 | 93 | 89 |
| 10 | 96 | 100 | 100 | 98 | 92 |
| 20 | 100 | 100 | 100 | 100 | 98 |

What is claimed is:

1. A process for the treatment of grasslands against grasshoppers or locusts comprising treating the grasslands attacked, or susceptible to attack, by grasshoppers or locusts with an effective amount of an active material which is 1-[2,6-dichloro-4-$CF_3$-phenyl]-3-cyano-4-$CF_3SO$-5-$NH_2$-pyrazole].

2. A process according to claim 1, comprising treating grasslands attacked or susceptible to attack by grasshoppers or locusts of the type Melanoplu supp. or of locusts of the type Schistocerca supp.

3. A process according to any one of claims 1, or 2, comprising treating grasslands using dilute compositions that contain 0.001 to 95% of active material.

4. A process according to any one of claims 1, or 2, comprising treating grasslands using a quantity of active material between 2 and 50 g/ha.

5. A process according to any one of claims 1, or 2, comprising treating grasslands using dilute compositions containing 0.2 to 15% of active material.

6. A process according to any one of claims 1, or 2, comprising treating grasslands using a quantity of active material between 3 g/ha and 20 g/ha.

7. A process according to claim 2, comprising treating grasslands attacked or susceptible to attack by Schistocerca gregaria or Chortoicetes terminifera.

* * * * *